(12) United States Patent
Miyoshi

(10) Patent No.: US 10,520,804 B2
(45) Date of Patent: Dec. 31, 2019

(54) PORTABLE RADIOGRAPHIC IMAGING APPARATUS

(71) Applicant: Konica Minolta, Inc., Tokyo (JP)

(72) Inventor: Kohei Miyoshi, Tokyo (JP)

(73) Assignee: Konica Minolta, Inc., Tokyo (JP)

( * ) Notice: Subject to any disclaimer, the term of this patent is extended or adjusted under 35 U.S.C. 154(b) by 113 days.

(21) Appl. No.: 15/815,794

(22) Filed: Nov. 17, 2017

(65) Prior Publication Data
US 2018/0143524 A1 May 24, 2018

(30) Foreign Application Priority Data
Nov. 18, 2016 (JP) .................. 2016-224681

(51) Int. Cl.
| | | |
|---|---|---|
| *G03B 42/02* | (2006.01) | |
| *A61B 6/00* | (2006.01) | |
| *G03B 42/04* | (2006.01) | |
| *A61B 6/10* | (2006.01) | |

(52) U.S. Cl.
CPC ............ *G03B 42/025* (2013.01); *A61B 6/102* (2013.01); *A61B 6/4283* (2013.01); *G03B 42/04* (2013.01); *A61B 6/4405* (2013.01)

(58) Field of Classification Search
None
See application file for complete search history.

(56) References Cited

U.S. PATENT DOCUMENTS

| | | | | |
|---|---|---|---|---|
| 2012/0213640 A1* | 8/2012 | Sanderson | .............. | B64C 3/185 416/226 |
| 2012/0270006 A1* | 10/2012 | McMillan | ............. | F01D 25/243 428/77 |
| 2015/0366524 A1* | 12/2015 | Suzuki | ................. | A61B 6/4283 378/189 |

FOREIGN PATENT DOCUMENTS

JP 2012-220659 A 11/2012

* cited by examiner

*Primary Examiner* — Hoon K Song
(74) *Attorney, Agent, or Firm* — Osha Liang LLP

(57) ABSTRACT

A portable radiographic imaging apparatus includes a sensor and a case that houses sensor panel. Radiation detector elements are arrayed two-dimensionally in the sensor panel. The case comprises a corner where two side walls are adjacent. The side walls are made of a continuous fiber reinforced resin that comprises one or more fiber layers oriented in a predetermined direction. The fiber layers are oriented in a direction from one to the other of the adjacent side walls in the corner. A breakpoint where the fiber layers are discontinuous over an entire thickness in a wall thickness direction is not present in an area of at least one of the corners.

15 Claims, 15 Drawing Sheets

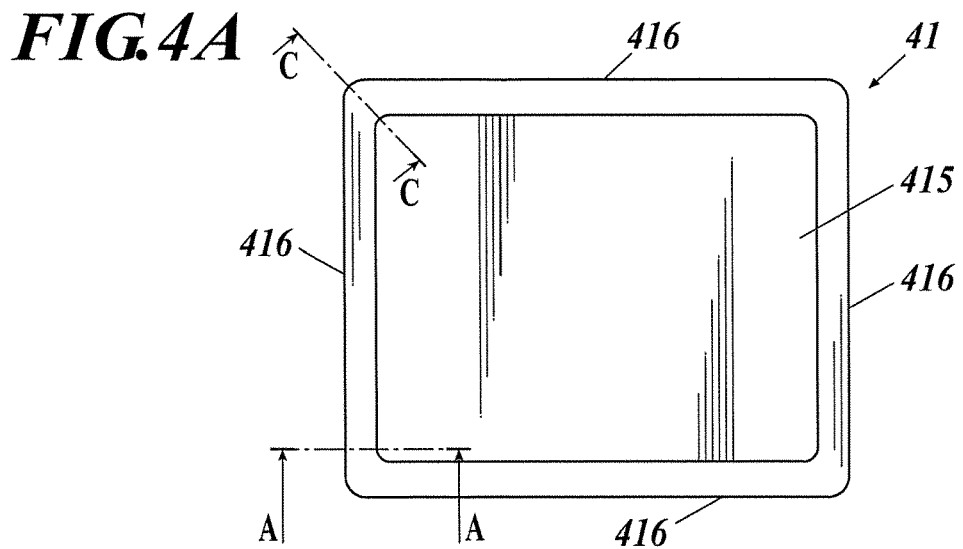
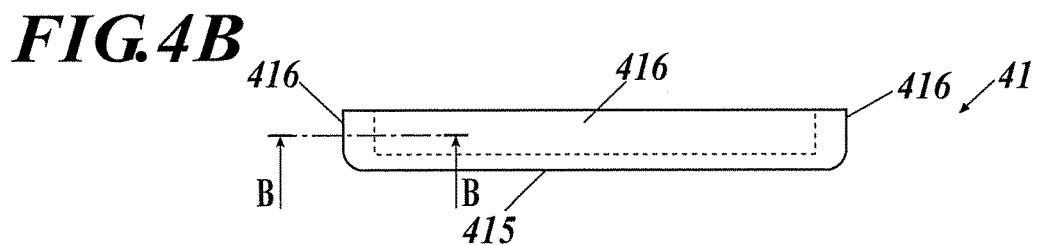
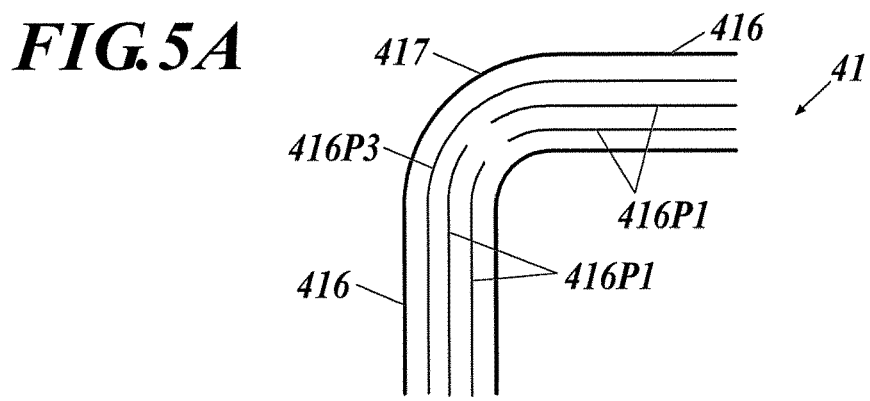
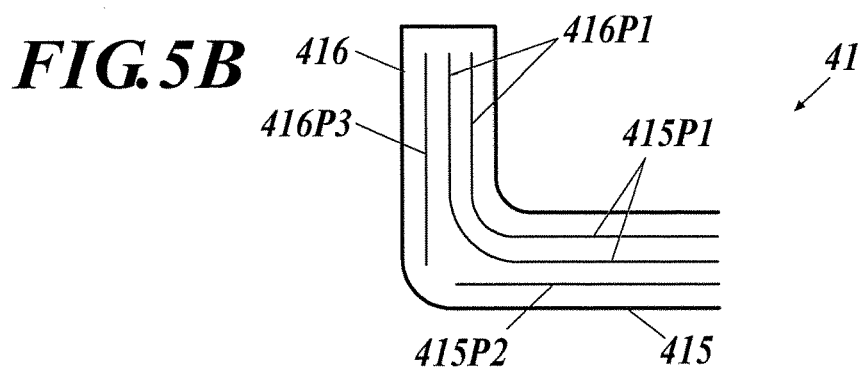

PORTABLE RADIOGRAPHIC IMAGING APPARATUS

PRIORITY

Japanese patent application No. 2016-224681 filed on Nov. 18, 2016, including description, claims, drawings, and abstract the entire disclosure is incorporated herein by reference in its entirety.

BACKGROUND

Technological Field

The present invention relates to a portable radiographic imaging apparatus.

Description of the Related Art

CR (Computed Radiography) cassettes containing a photostimulable phosphor sheet for storing radiation energy transmitted through a subject have been widely used as radiographic imaging apparatuses for diagnosis of an illness.

In recent years, as a substitute for such screen/film cassettes and CR cassettes, an alternative radiographic imaging apparatus with two-dimensionally arrayed radiation detector elements (in a matrix) (flat panel detector, also referred to as a semiconductor imaging sensor) has been developed, in which electric charges are generated by the respective radiation detector elements according to the dose of radiation radiated through a subject, and the electric charges thus generated are read out as signals. Further, portable radiographic imaging apparatuses (also referred to as FPD cassettes or the like) have also been developed in which a sensor panel with arrayed radiation detector elements is housed in a case.

Since such portable radiographic imaging apparatuses are highly portable and may sometimes be subjected to a drop impact or the like in use, it is necessary to protect them from such impacts.

Focusing on that such apparatuses often fall in a corner of the case first, conventional radiographic imaging apparatuses have recesses that are formed in the inner corners of the case to avoid contact with the corners of a base mount supporting an inner substrate so as to reduce collision between the inside of the case and the base mount (e.g. see JP 2012-220659A).

However, there is decreased rigidity and decreased strength because the walls of the corners are thinned due to the recesses formed in the inner corners of the side walls of the case.

SUMMARY

One or more embodiments of the present invention provide a portable radiographic imaging apparatus with the reinforced corners of a case that are likely to be subjected to a drop impact.

According to one or more embodiments of the present invention, there is provided a portable radiographic imaging apparatus; including:
a sensor panel in which radiation detector elements are arrayed two dimensionally; and
a case in which the sensor panel is housed,
wherein the case comprises a corner at which two side walls are adjacent,
wherein the side walls are made of a continuous fiber reinforced resin that comprises one or more fiber layers oriented in a certain direction,
wherein the fiber layers of the continuous fiber reinforced resin are oriented in a direction from one to the other of the adjacent side walls in the corner, and
wherein a breakpoint where the fiber layers are discontinuous over an entire thickness in a wall thickness direction is not present in an area of at least one of the corner.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, and wherein:

FIG. 4A is a plan view of a front plate of a case, in accordance with one or more embodiments;

FIG. 4B is a side view of the front plate of the case, in accordance with one or more embodiments;

FIG. 5A is a partial cross-sectional view of the front plate taken along the line B-B of FIG. 4B, in accordance with one or more embodiments;

FIG. 5B is a partial cross-sectional view of the front plate taken along the line A-A of FIG. 4A, in accordance with one or more embodiments;

DETAILED DESCRIPTION OF EMBODIMENTS

Figure 1:
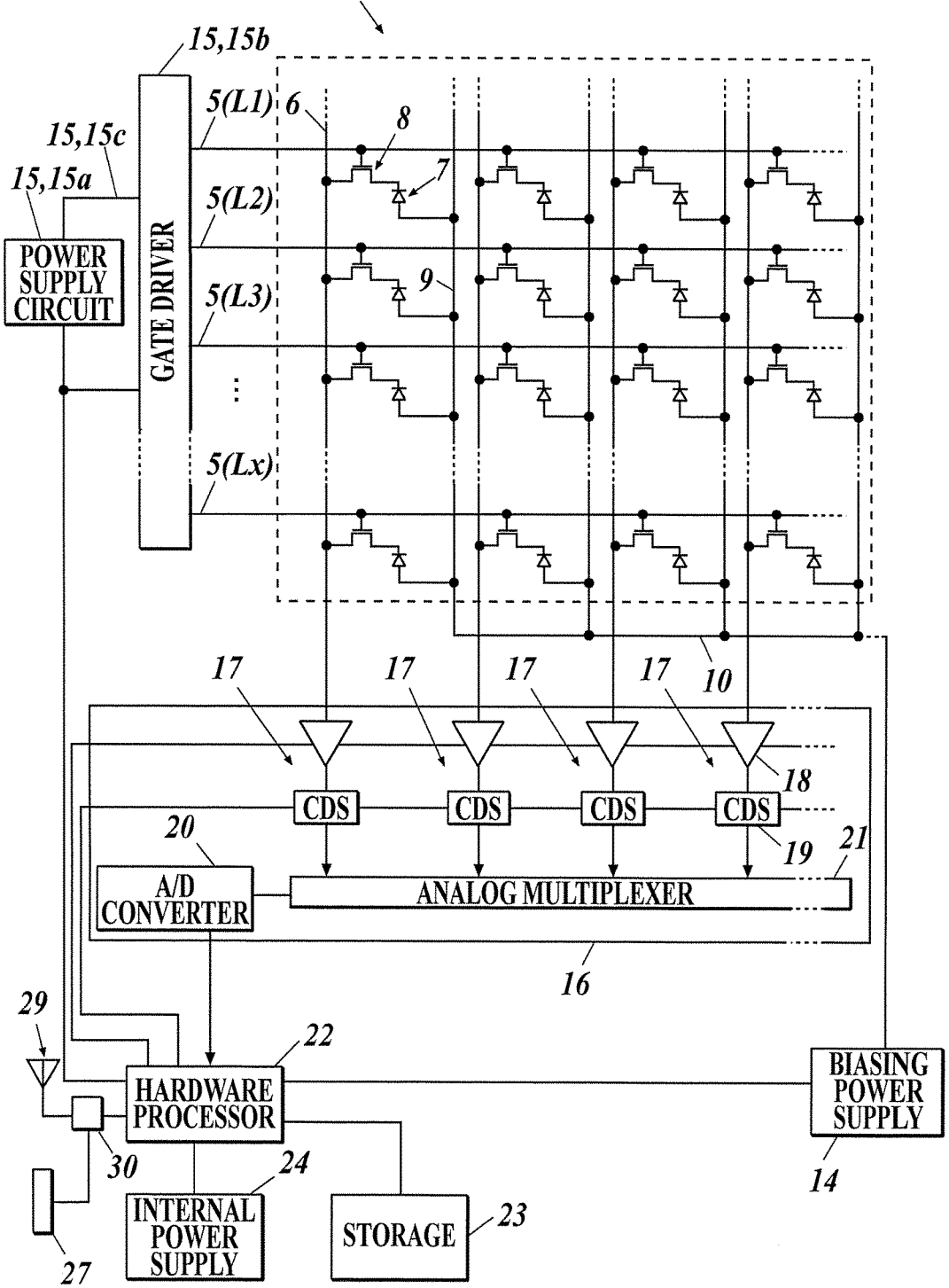
FIG. 1 is a block diagram of an equivalent circuit of a portable radiographic imaging apparatus according to one or more embodiments of the present invention.

Hereinafter, one or more embodiments of the present invention will be described with reference to the drawings. However, the scope of the invention is not limited to the disclosed embodiments.

A portable radiographic imaging apparatus according to one or more embodiments of the present invention will be described referring to the drawings.

In the following description, a portable radiographic imaging apparatus is also referred to simply as a radiographic imaging apparatus. Further, while the following description is related to a so-called indirect radiographic imaging apparatus that includes a scintillator and the like to convert radiation into electromagnetic wave with a different wavelength such as visible light so as to output an electric signal, one or more embodiments of the present invention are also applicable to so-called direct radiographic imaging apparatuses that directly detect radiation by means of a radiation detector element without a scintillator or the like.

Circuit Configuration, Etc. of Radiographic Imaging Apparatus

First, the circuit configuration of the radiographic imaging apparatus 1 according to one or more embodiments of the present invention will be described. FIG. 1 is a block diagram of an equivalent circuit of the radiographic imaging apparatus 1 according to one or more embodiments. As illustrated in FIG. 1, the radiographic imaging apparatus 1 includes a sensor substrate 51 (see FIG. 3 described below) and radiation detector elements 7 that are arrayed two-dimensionally (in a matrix) on the sensor substrate 51.

Biasing lines 9 are connected to the respective radiation detector elements 7 so that a reverse-biasing voltage is applied from a biasing power supply 14 through the biasing lines 9 and the connection lines 10 thereof. TFTs (Thin Film Transistors) 8 as switching elements are connected to the respective radiation detector elements 7 and to signal lines 6.

A scanning driver 15 switches the output voltage between ON voltage and OFF voltage supplied from a power supply circuit 15a through a wiring 15c by means of a gate driver 15b and applies it to lines L1 to Lx of scanning lines 5. When the OFF voltage is applied through the scanning lines 5, the TFTs 8 turns off to break electric connection between the radiation detector elements 7 and the signal lines 6 so that electric charges are accumulated in the radiation detector elements 7. When the ON voltage is applied through the scanning line 5, the TFTs 8 turns on so that the electric charges accumulated in the radiation detector elements 7 are discharged to the signal lines 6.

The signal lines 6 are connected to respective reader circuits 17 in a reader IC 16. In a process of reading out signals D, when the ON voltage is applied to a certain line L of the scanning lines 5 from the gate driver 15b, corresponding TFTs 8 are turned on. Then, electric charges are flown to the reader circuits 17 from corresponding radiation detector elements 7 through the TFTs 8 and the signal lines 6, and voltages according to the input of the respective electric charges are output from an amplifier circuit 18.

A correlated double sampling circuit 19 (denoted as "CDS" in FIG. 1) reads the voltages output from the amplifier circuit 18 and outputs corresponding analog signals D. In this way, in one or more embodiments, the reader circuits 17 of the reader IC 16 read the electric charges generated in the radiation detector elements 7 according to the dose of radiation and outputs them as the signals D.

The signals D output from the amplifier circuit 18 are sequentially sent to an A/D converter 20 through an analog multiplexer 21. The signals D are sequentially converted to corresponding digital signal values by means of the A/D converter 20 and sequentially stored in a storage 23. In one or more embodiments, the gate driver 15b of the scanning driver 15 applies the ON voltage sequentially to the lines L1 to Lx of the scanning lines 5 in the reading process so that the signals D are read out from all radiation detector elements 7.

The hardware processor 22 includes a computer in which a CPU (Central Processing Unit), a ROM (Read Only Memory), a RAM (Random Access Memory), an input/output interface and the like are connected through a bus, an FPGA (Field Programmable Gate Array) and the like, which are not shown in the figure. The hardware processor 22 may be constituted by a dedicated controller circuit.

The hardware processor 22 is connected to a storage 23 constituted by an SRAM (Static RAM), an SDRAM (Synchronous DRAM), a NAND flash memory or the like and an internal power supply 24 constituted by a lithium-ion capacitor or the like. The hardware processor 22 is also connected to a communicator 30 that performs wired or wireless communication with external devices though an antenna 29 and a connector 27

As described above, the hardware processor 22 controls application of a reverse biasing voltage from the biasing power supply 14 to the radiation detector elements 7 and the operation of the scanning driver 15 and the reader circuit 17 so as to perform the above-described process of reading the signals D from the radiation detector elements 7, to store the read signal values D in the storage 23 and to transfer the stored signal values D to an external device through the communicator 30.

Configuration of Portable Radiographic Imaging Apparatus

Figure 2:
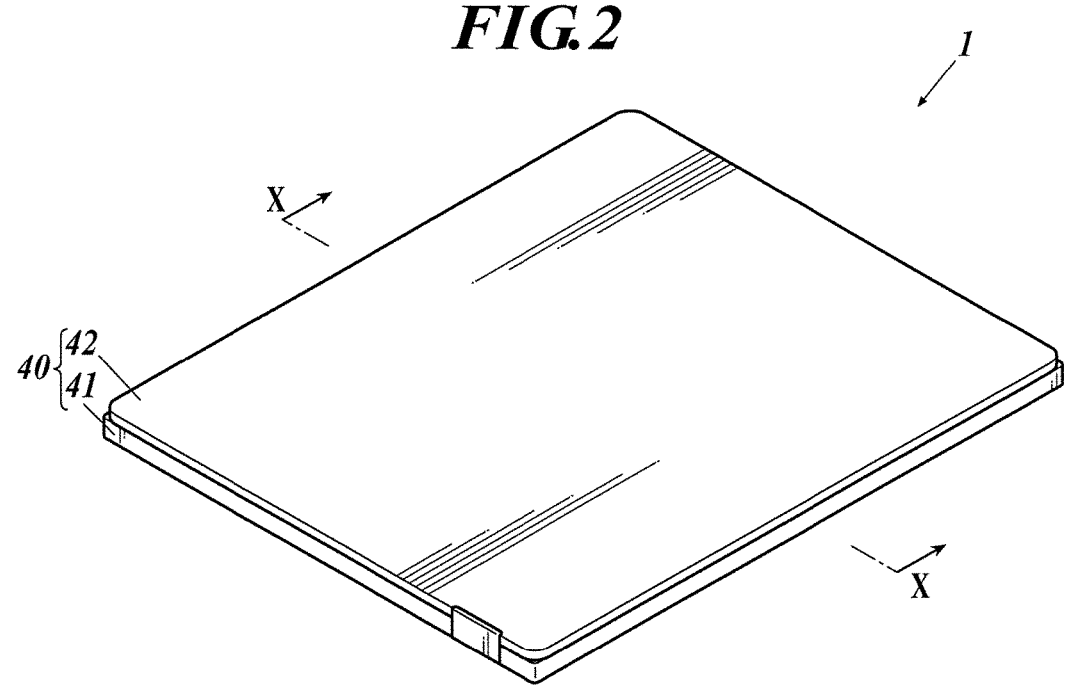
FIG. 2 is a perspective view of the portable radiographic imaging apparatus, in accordance with one or more embodiments.
Figure 3:
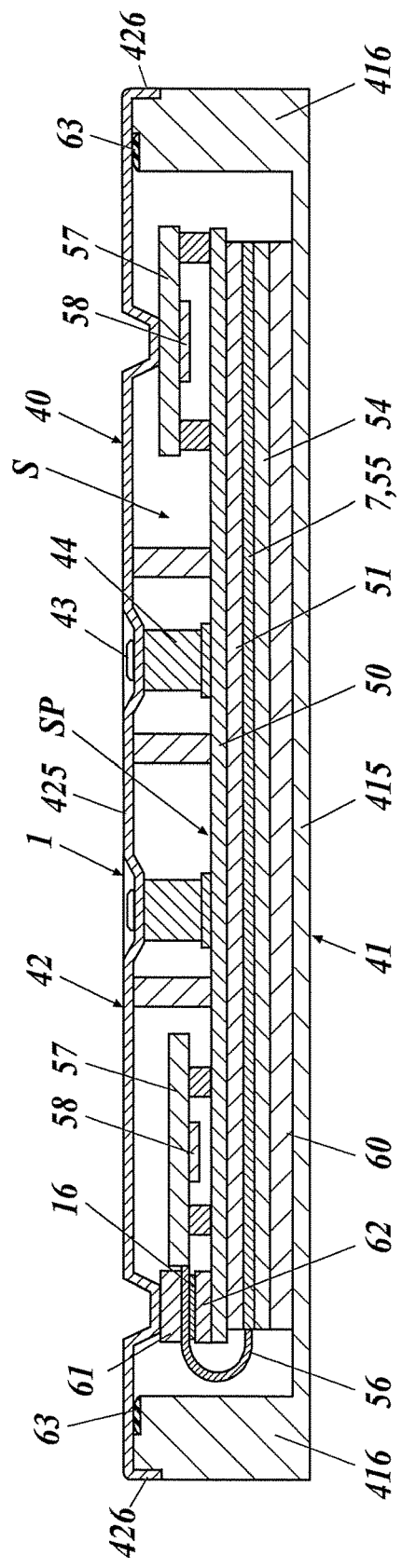
FIG. 3 is a cross-sectional view of the portable radiographic imaging apparatus taken along the line X-X in FIG. 2, in accordance with one or more embodiments.

FIG. 2 is a perspective view illustrating the configuration of the portable radiographic imaging apparatus 1 according to one or more embodiments, and FIG. 3 is a cross-sectional view of the portable radiographic imaging apparatus 1 taken along the line X-X in FIG. 2. For ease of understanding the internal configuration, the thickness in the height direction in FIG. 3 is illustrated greater than in reality.

As illustrated in FIG. 3, the radiographic imaging apparatus 1 includes a case 40 and a sensor panel SP (also referred to as a TFT panel) that is housed in the case 40. In FIG. 3, the radiographic imaging apparatus 1 is placed such that an incident plate 415 where radiation is emitted faces downward. In the following description, the height direction of the radiographic imaging apparatus 1 is based on the position of the radiographic imaging apparatus 1 as illustrated in FIG. 3.

In one or more embodiments, the case 40 of the radiographic imaging apparatus 1 is composed mainly of a front plate 41 as a front member and a back plate 42 as a back member, in which the front plate 41 includes the incident plate 415 that is formed approximately in a rectangular flat plate and side walls 416 that are erected along the four sides of the peripheral edge of the incident plate 415, and the back plate 42 includes a bottom plate 425 that is formed approximately in a rectangular flat plate opposed to the incident plate 415 and side walls 426 that are erected along the four sides of the outer peripheral edge of the bottom plate 425.

In one or more embodiments, the front plate 41 is made of, for example, continuous fiber reinforced resin such as CFRP (Carbon Fiber Reinforced Plastic), and the incident plate 415 and the side walls 416 of the front plate 41 are integrally formed by autoclave molding, thermal pressing, RTM (Resin Transfer Molding) or the like.

The back plate 42 is made of, for example, a metal with high specific strength and high heat dissipation, specifically a magnesium alloy (e.g. AZ31 sheet for pressing), and the bottom plate 425 and the side walls 426 of the back plate 42 are integrally formed by pressing. In terms of specific strength and heat dissipation, the back plate 42 may also be made of an aluminum alloy (e.g. A5052).

The back plate 42 is attached to the side walls 416 of the front plate 41 and pillars 44 that protrude from a base mount 50 (described later) of the sensor panel SP toward the back plate 42 by means of screws 43 as engaging members (not shown in FIG. 2). The back plate 42 is coupled to the front plate 41 to form a box shape.

Between the back plate 42 and the front plate 41, a packing 63 is intervened to ensure the hermetic and watertight property of the case 40.

The structure of the front plate 41 and the back plate 42 of the case 40 will be described later in detail.

In one or more embodiments, the sensor panel SP is formed as follows. In the following description, the faces of the components of the radiographic imaging apparatus 1 that are opposed to the incident plate 415 of the front plate 41 (i.e. the downside faces in FIG. 3) are referred to as front faces, and the faces opposed to the back plate 42 (i.e. the upside faces in FIG. 3) are referred to as back faces.

Unless otherwise noted, the portion of the case 40 at the side of the back plate 42 is defined as an upper portion, and the portion at the side of the front plate 41 is defined as a lower portion. Further, the height direction based on the definition is also referred to as a thickness direction.

The sensor panel SP includes the base mount 50 that includes a metal layer (not shown) of lead or the like for shielding against radiation. On the front face of the base mount 50, the sensor substrate 51 constituted by a glass substrate or the like is disposed. On the front face of the sensor substrate 51, the radiation detector elements 7 and the like are arrayed two dimensionally.

The scintillator 55 is formed on one face of a scintillator substrate 54 constituted by a glass substrate or the like. In one or more embodiments, the sensor substrate 51 and the scintillator substrate 54 are disposed such that the scintillator 55 and the radiation detector elements 7 are opposed to each other. The sensor substrate 51 and the scintillator substrate 54 are bonded to each other by adhesive (not shown) in the portions outside the radiation detector elements 7, the scintillator 55 and the like.

The signal lines 6 (see FIG. 1) and the like wired on the sensor substrate 51 are connected to a flexible circuit board 56 in which chips including the reader IC 16 are mounted on a film. The flexible circuit board 56 extends to the back face of the base mount 50 where it is connected to a PCB 57 and the like.

On the PCB 57, circuits and electronic components of the hardware processor 22, the storage 23 (see FIG. 1) and the like (hereinafter referred to collectively as electronic equipment 58) are mounted. In FIG. 3, the electronic equipment 58 is mounted on the front face of the PCB 57. However, the electronic equipment 58 may be mounted on the back face (or both the front and back faces) of the PCB 57 instead.

In the radiographic imaging apparatus 1 according to one or more embodiments, the sensor panel SP is configured as described above. Since the electronic equipment 58 is disposed on the back face of the sensor panel SP, i.e. on the side opposed to the back plate 42, the electronic equipment 58 becomes accessible only by detaching the back plate 42 (i.e. without taking out the sensor panel SP from the case 40). Accordingly, the electronic equipment 58 can be replaced readily.

As illustrated in FIG. 3, a spacer 60 is disposed between the scintillator substrate 54 and the front plate 41. In one or more embodiments, a heat conductive member 61 is disposed between the reader IC 16 and the back plate 42 to conduct heat generated in the reader IC 16 to the back plate 42 and to dissipate it to the outside from the back plate 42. Further, a heat insulating member 62 is disposed between the reader IC 16 and the base mount 50 of the sensor panel SP so that heat generated in the reader IC 16 is not conducted to the sensor panel SP.

Detailed Structure of Case

Next, the structure of the case 40 will be described in detail based on FIG. 4A to FIG. 6C. FIG. 4A is a plan view of the front plate 41 of the case 40, and FIG. 4B is a front view thereof. FIG. 5A is a partial cross-sectional view taken along the line B-B in FIG. 4B, and FIG. 5B is a partial cross-sectional view taken along the line A-A in FIG. 4A.

The front plate 41 includes the incident plate 415 having a rectangular flat plate shape and the four side walls 416 erected from the four sides of the incident plate 415. The side walls 416 are connected to the respective adjacent side walls at the four corners 417.

The "height direction (thickness direction)" of the case 40, the front plate 41 and the back plate 42 refers to the direction parallel to the incident direction of radiation in the radiographic imaging apparatus 1.

The "outside" of a corner of the case 40, the front plate 41 and the back plate 42 refers to an area toward which the corner protrudes, and the "inside" of a corner refers to an area between the two side walls 416 connected at the corner.

The incident plate 415 and the side walls 416 of the front plate 41, which have a plate shape, are all made of CFRP, which is a continuous fiber reinforced resin having an oriented carbon fiber layer.

The CFRP used in the incident plate 415 and the side walls 416 is in a sheet form when in the state of an unmolded intermediate material, in which fiber filaments of oriented fiber are woven in mutually perpendicular two directions into a reticular pattern, and the fabric thus formed is impregnated with thermoset epoxy resin. The sheet material is laminated and formed into the shape of the front plate 41 as illustrated in FIG. 4A and FIG. 4B by autoclave molding or heat pressing. The sheet material has a layer in which carbon fiber is oriented independently in mutually perpendicular two directions.

Accordingly, in the incident plate 415 and the side walls 416, oriented carbon fiber layers are laminated in the wall thickness direction.

The front plate 41 of the case 40 of the radiographic imaging apparatus 1 according to one or more embodiments has a feature with regard to the fiber orientation direction of the carbon fiber layers, and the front plate 41 will be described in detail in light of the feature.

In the following description, the phrase "a carbon fiber layer is oriented parallel to a certain direction" or "a carbon fiber layer is oriented in a certain direction" means that either one of the mutually perpendicular two orientation directions of the carbon fiber layer is parallel to or in the certain (i.e., predetermined) direction.

Parts of Front Plate

Figure 6A:
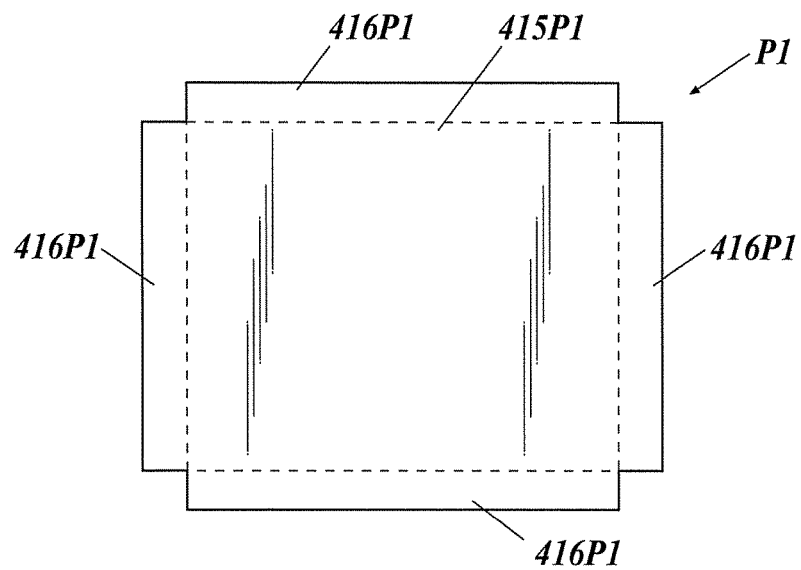
FIG. 6A is a plan view of a first part of CFRP sheet for forming the front plate, in accordance with one or more embodiments.
Figure 6B:
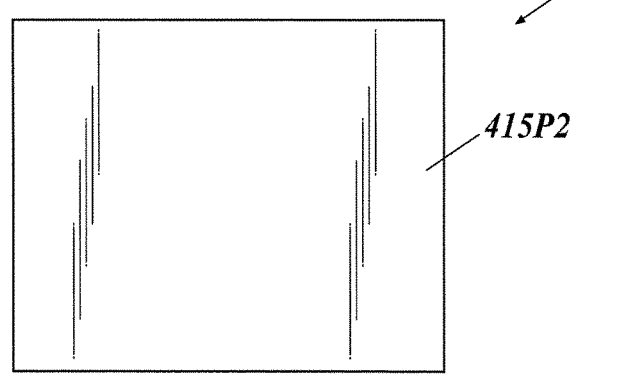
FIG. 6B is a plan view of a second part of CFRP sheet for forming the front plate, in accordance with one or more embodiments.
Figure 6C:
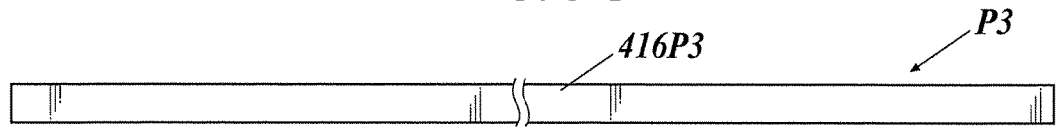
FIG. 6C is a plan view of a third part of CFRP sheet for forming the front plate, in accordance with one or more embodiments.

FIG. 6A to FIG. 6C are plan views of parts P1 to P3 of CFRP sheet for forming the front plate 41.

Since the incident plate 415 and the side walls 416 of the front plate 41 has the same thickness, the number of parts P1 to P3 are suitably selected so that they are uniformly laminated in the incident plate 415 and the side walls 416.

The number of laminated sheets is not particularly limited, and one or more embodiments described above are examples in which three sheets are laminated to form a three-layer structure.

The part P1 includes a rectangular incident plate forming part 415P1 that forms the incident plate 415 of the front plate 41 and side wall forming parts 416P1 that are continuously adjacent respectively to the four sides of the incident plate forming part 415P1 to form the side walls 416.

Since the side wall forming parts 416P1 are continuously adjacent to the four sides of the incident plate forming part 415P1, they can be vertically erected with respect to the incident plate forming part 415P1 by bending them along the four sides. The part P1 can thus be formed into a similar shape to the front plate 41.

To form the front plate 41, two parts P1 are laminated such that they completely match.

Since the incident plate forming part 415P1 and the side wall forming parts 416P1 are originally constituted by the same single CFRP sheet, the carbon fiber of the internal layer is continuous without any break.

Further, since a CFRP sheet includes carbon fiber filaments that are woven in a grid pattern in mutually perpendicular two directions as described above, the part P1 includes carbon fiber oriented in the mutually perpendicular two directions.

The part P1 is formed such that the layered carbon fiber is oriented parallel to the long and short sides of the incident plate forming part 415P1.

The part P2 is composed only of a rectangular incident plate forming part 415P2 for forming the incident plate 415.

To form the front plate 41, one part P2 is laminated under the incident plate forming parts 415P1 of the parts P1.

Further, the part P2 is formed such that the layered carbon fiber is oriented parallel to the long and short sides of the incident plate forming part 415P2.

The part P3 includes a rectangular side wall forming part 416P3 for forming the four side walls 416 of the front plate 41.

The part P3 has a strip shape with a length corresponding to the sum of the longitudinal lengths of the four side walls 416 and approximately the same width as the height of the front plate 41.

The part P3 is formed such that the layered carbon fiber is oriented respectively parallel to the long and short sides of the side wall forming part 416P3.

The part P3 is disposed to wrap around the outer faces of the four side wall forming parts 416P1 that are bent and erected along the four sides of the incident plate forming part 415P1 of the part P1. In the wrapped position, one and the other ends of the part P3 are closely opposed to each other, and they are coupled to each other with epoxy resin by subsequent autoclave molding or heat pressing. However, inside the part P3, the carbon fiber layer oriented parallel to the longitudinal direction of the part P3 is not coupled but remain discontinuous.

The part P3 is disposed on the outer face of the four side wall forming parts 416P1 of the part P1 such that the coupling portion between one and the other ends thereof is located apart from the four corners 417 of the front plate 41.

Cross-Sectional Structure of Front Plate

The front plate 41, which is formed by combining the parts P1 to P3 as described above, has cross sections as illustrated in FIG. 5A and FIG. 5B. In FIG. 5A and FIG. 5B, hatching to epoxy resin in the cross sections is omitted for the purpose of clearly depicting the structure. This applies to the other cross-sectional views.

In the boundary area between the incident plate 415 and the side walls 416 of the front plate 41, three carbon fiber layers oriented in the direction from the incident plate 415 to the side walls 416 are formed as illustrated in FIG. 5B. Among them, the inner two carbon fiber layers (These are denoted as 415P1, 416P1 in FIG. 5B for descriptive purpose. This applies to the other cross-sectional views.) are derived from the continuous carbon fiber layers of the incident plate forming parts 415P1 and the side wall forming parts 416P1 of the parts P1. Accordingly, the carbon fiber layers are continuous even after autoclave molding or heat pressing of the front plate 41.

Since the carbon fiber layers of the incident plate 415 extend to the side walls 416 joined to the incident plate 415 as described above, the tensile strength of the carbon fiber can be utilized to maintain the joining between the incident plate 415 and the side walls 416. Therefore, the strength of the case can be improved.

Among the three carbon fiber layers, the outer carbon fiber layer is derived from the carbon fiber layer of the incident plate forming part 415P2 of the part P2 and the carbon fiber layer of the side wall forming part 416P3 of the part P3. While the part P3 is used in a part of the side walls 416 in order to improve the strength of the corners 417, the part P2 can adjust the wall thickness to equalize the wall thickness of the incident plate 415 and the side walls 416.

In the corners 417 of the front plate 41, three carbon fiber layers are formed, which are oriented in the direction from one to the other of side walls 416 adjacent across a corner 417 as illustrated in FIG. 5A.

Among them, the inner two carbon fiber layers are derived from the originally discontinuous carbon fiber layers of the side wall forming parts 416P1 at two sides of parts P1. Accordingly, these carbon fiber layers remain discontinuous even after the front plate 41 is molded.

In contrast, in the cross section of the corners 417 of the front plate 41, since the outermost carbon fiber layer is derived from the continuous carbon fiber layer of the side wall forming part 416P3 of the part P3, the carbon fiber layer remains continuous after the front plate 41 is molded.

Accordingly, one of the carbon fiber layers in the corners 417 of the front plate 41 is continuous over the entire areas of the corners 417 (in the direction from one side wall 416 to the other side wall 416). Therefore, a breakpoint B (see FIG. 7) where the carbon fiber layers are discontinuous over the entire thickness in the wall thickness direction is not formed in the areas of the corners 417.

It is desirable that a breakpoint B where carbon fiber layers are discontinuous is not formed over the entire length in the height direction of the corners 417. This applies to one or more embodiments of the present invention described below.

Figure 7:
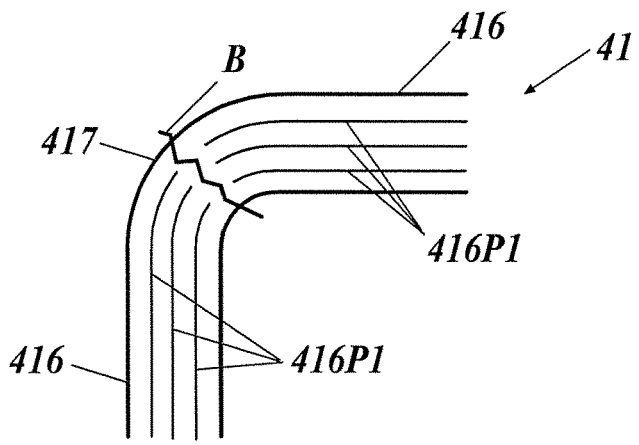
FIG. 7 is a cross-sectional view of a front plate for comparison taken along the line B-B of FIG. 4B, in accordance with one or more embodiments.

For comparison, FIG. 7 illustrates a cross section of a corner 417 of a front plate 41 that is formed by laminating three parts P1.

Also in this case, three carbon fiber layers are formed in the corners 417 of the front plate 41, in which the carbon fiber is oriented in the direction from one to the other of side walls 416 adjacent across a corner 417.

Since all carbon fiber layers are derived from the originally discontinuous side wall forming parts 416P1 at two sides of the parts P1, the carbon fiber layers remain discontinuous even after the front plate 41 is molded.

As a result, in the front plate 41 for comparison, breakpoints B are formed in the areas of the respective corners 417, where the carbon fiber layers are discontinuous over the entire thickness in the wall thickness direction.

In this case, the tensile strength of the corners 417 of the front plate 41 is provided only by epoxy resin. Therefore, sufficient strength cannot be achieved.

When a breakpoint B is formed as illustrated in FIG. 7, the achievable tensile strength is as low as 50 to 120 MPa in the breakpoint B. In contrast, when even a single carbon fiber layer is continuous as illustrated in FIG. 5A, it is possible to remarkably improve the tensile strength of the corners 417 since the tensile strength of a continuous carbon fiber is as high as 600 to 800 MPa.

Area of Corner

The term "the area of a corner", as used herein, is defined as follows.

Figure 8A:
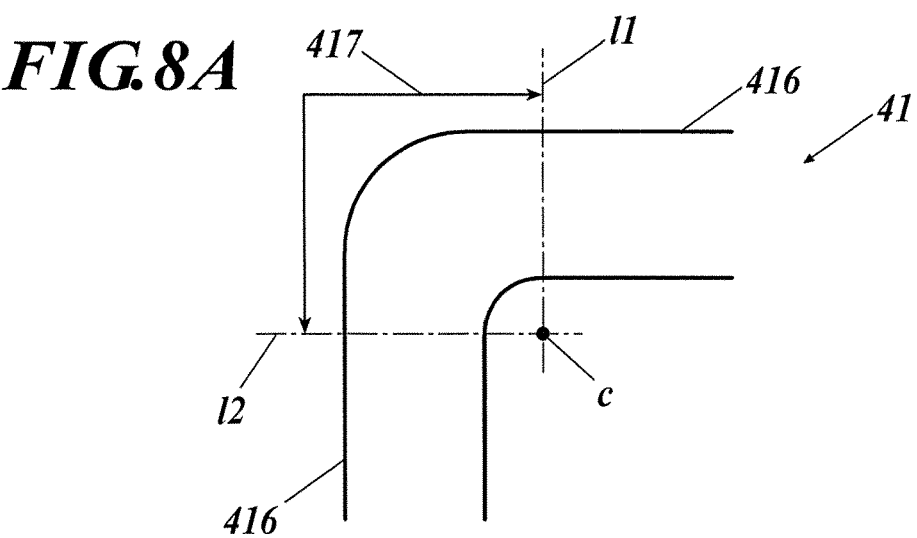
FIG. 8A illustrates the corner area of a case having an arcuate inner side, in accordance with one or more embodiments.

When the inner side of a corner 417 is formed in an arcuate shape in an angle of 90° in a plan view as illustrated in FIG. 8A, the "area of the corner" is defined as the area in an angle of 90° between a line l1 through a reference point c parallel to one of the side walls 416 adjacent to the corner 417 and a line l2 through the reference point c parallel to the other of the side walls 416, where the reference point c is the center of the arcuate shape.

The "wall thickness direction" in the corner 417 corresponds to the radial direction about the reference point c.

Figure 8B:
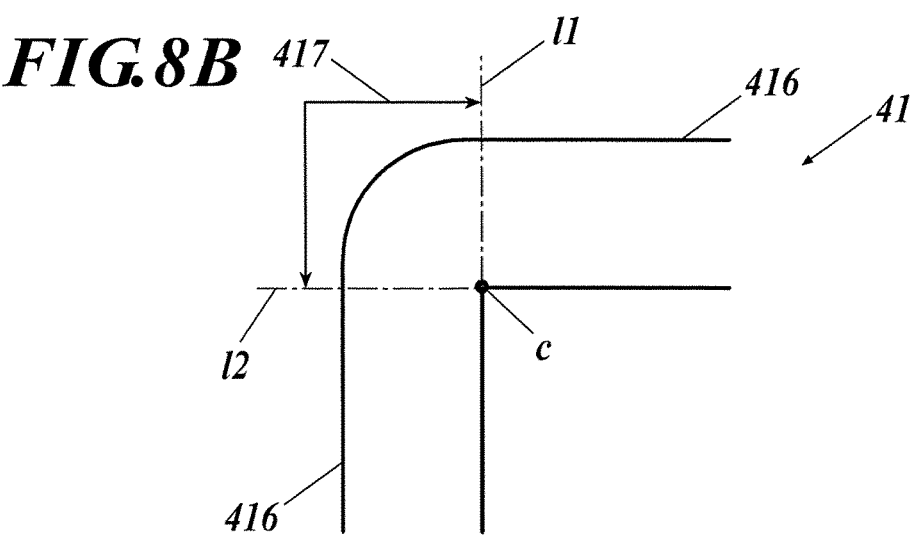
FIG. 8B illustrates the corner area of a case having an inner side sharply bent at a right angle, in accordance with one or more embodiments.

When the inner side of a corner 417 is formed not in an arcuate shape but in a perpendicular bent shape as illustrated in FIG. 8B, the "area of the corner" is defined as the area in an angle of 90° between a line l1 through a reference point c parallel to one of the side walls 416 adjacent to the corner 417 and a line l2 through the reference point c parallel to the other of the side walls 416, where the reference point c is the intersection of the inner faces of the side walls 416.

The "wall thickness direction" corresponds to the radial direction about the reference point c.

Another Example of Parts for Forming Front Plate (1)

Figure 9A:
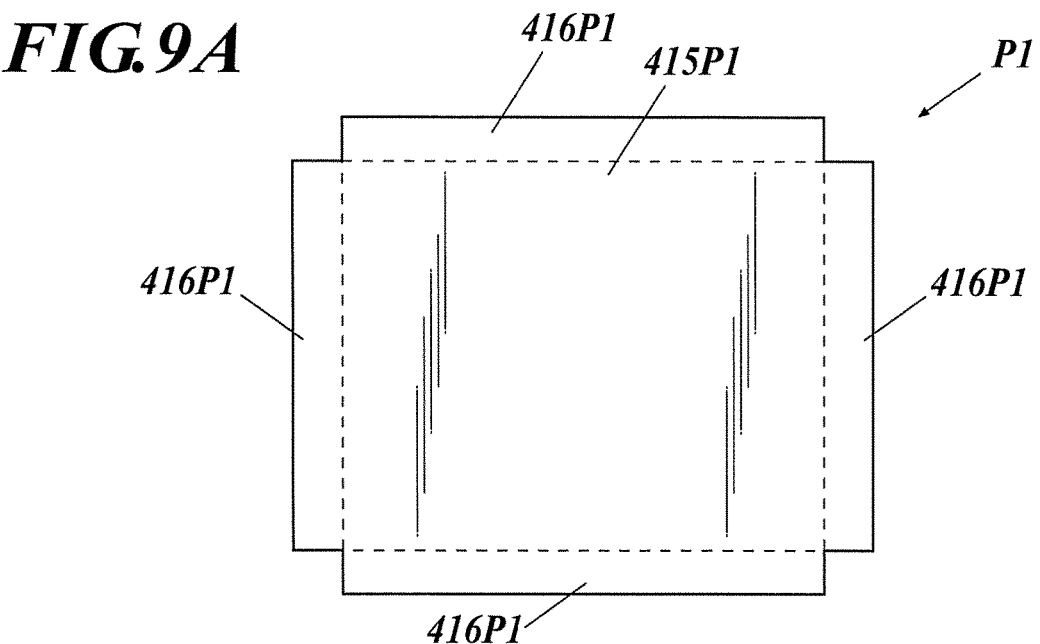
FIG. 9A is a plan view of a first part of another combination of CFRP sheet for forming the front plate, in accordance with one or more embodiments.
Figure 9B:
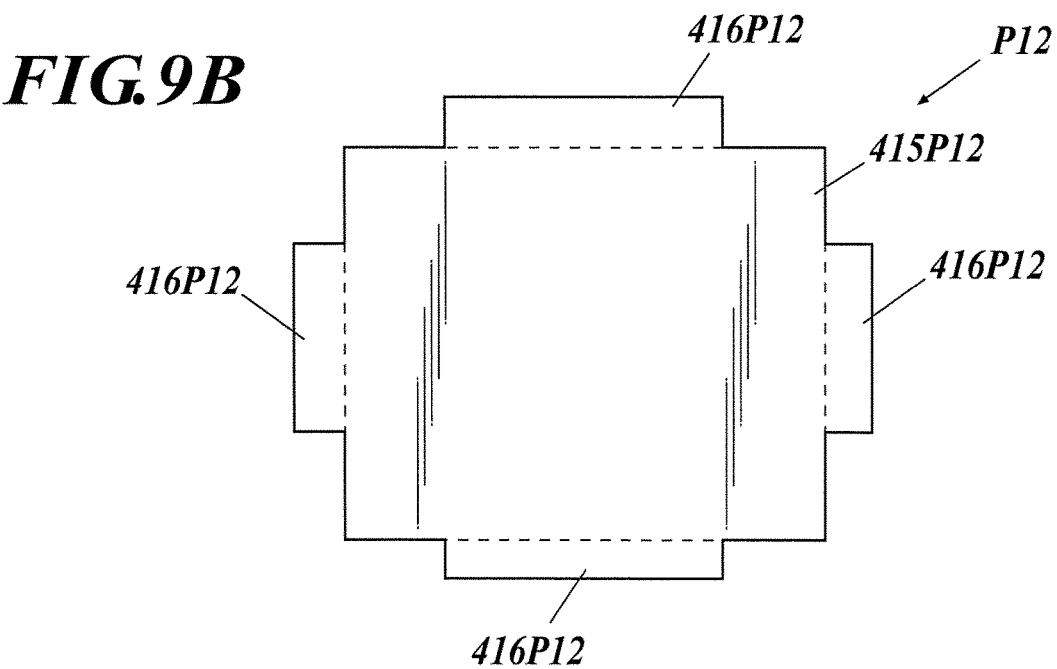
FIG. 9B is a plan view of a second part of another combination of CFRP sheet for forming the front plate, in accordance with one or more embodiments.
Figure 9C:
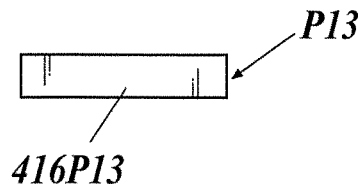
FIG. 9C is a plan view of a third part of another combination of CFRP sheet for forming the front plate, in accordance with one or more embodiments.

FIG. 9A to FIG. 9C illustrate the nets of parts P1, P12, P13 of CFRP sheet, which are another example of parts for forming the front plate 41.

When the parts P1, P12, P13 are used, the front plate 41 also has a three-layer structure with uniform thickness of the incident plate 415 and the side walls 416.

The part P1 is identical to the above-described part P1, and the description thereof is omitted.

The part P12 includes a rectangular incident plate forming part 415P12 that forms the incident plate 415 of the front plate 41 and side wall center forming parts 416P12 that are continuously adjacent respectively to the four sides of the incident plate forming part 415P12 to form the center parts of the side walls 416.

Since the side wall center forming parts 416P12 are continuously adjacent to the center parts of the four sides of the incident plate forming part 415P12, they can be vertically erected with respect to the incident plate forming part 415P12 by bending them along the four sides. The part 416P12 can thus be formed into a similar shape to the front plate 41.

Further, the part P12 is formed such that the layered carbon fiber is oriented parallel to the long and short sides of the incident plate forming part 415P12.

To form the front plate 41, one part P12 is laminated under the incident plate forming parts 415P1 of two parts P1.

The part P13 includes a side wall end forming part 416P13 that forms the adjacent ends of two side walls 416 adjacent across a corner 417 of the front plate 41. Since the part P13 is used in each of the four corners 417, four parts P13 are used to form the front plate 41.

The part P13 has a strip shape with a length corresponding to one fourth of the remainder of subtracting the sum of the lengths of the four side wall center forming parts 416P12 of the part P12 from the sum of the lengths of the four side walls 416 and approximately the same width as the height of the front plate 41.

The parts P13 are formed such that the layered carbon fiber is oriented respectively parallel to the long and short sides of the side wall forming part 416P3.

The parts P13 are disposed at the corners 417 to fill the gaps between adjacent side wall center forming parts 416P12 when the four side wall center forming parts 416P12 are bent and erected along the four sides of the incident plate forming part 415P12 of the part P12.

By the above-described arrangement, the part P12 and the four parts P13 together can be formed into the same three-dimensional shape as the parts P1, and the front plate 41 can be formed by laminating them with the two parts P1 and subjecting them to autoclave molding or heat pressing.

Also in this example, the corners 417 can be formed to have the cross-sectional structure as illustrated in FIG. 5A, and the incident plate 415 and the side walls 416 can be formed to have a uniform wall thickness.

Another Example of Parts for Forming the Front Plate (2)

Figure 10A:
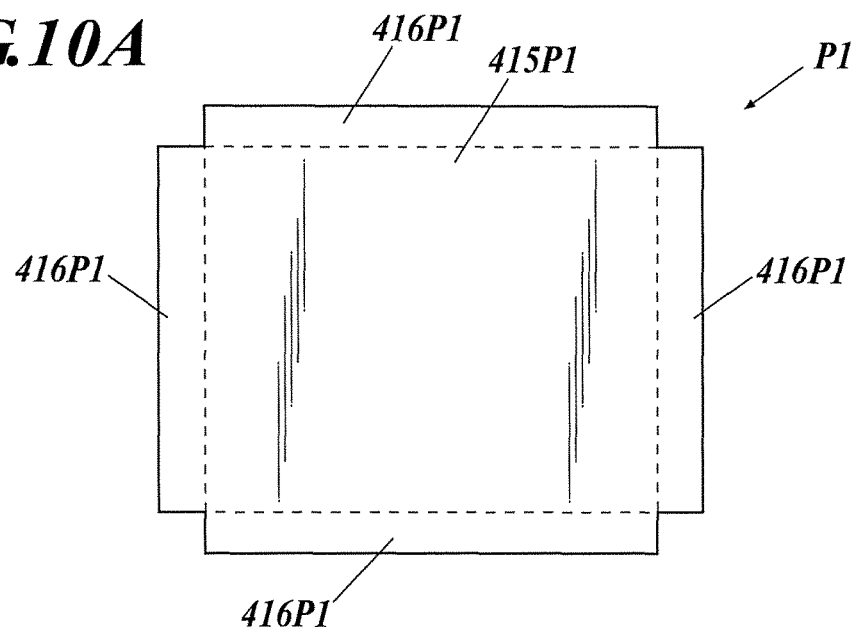
FIG. 10A is a plan view of a first part of yet another combination of CFRP sheet for forming the front plate, in accordance with one or more embodiments.
Figure 10B:
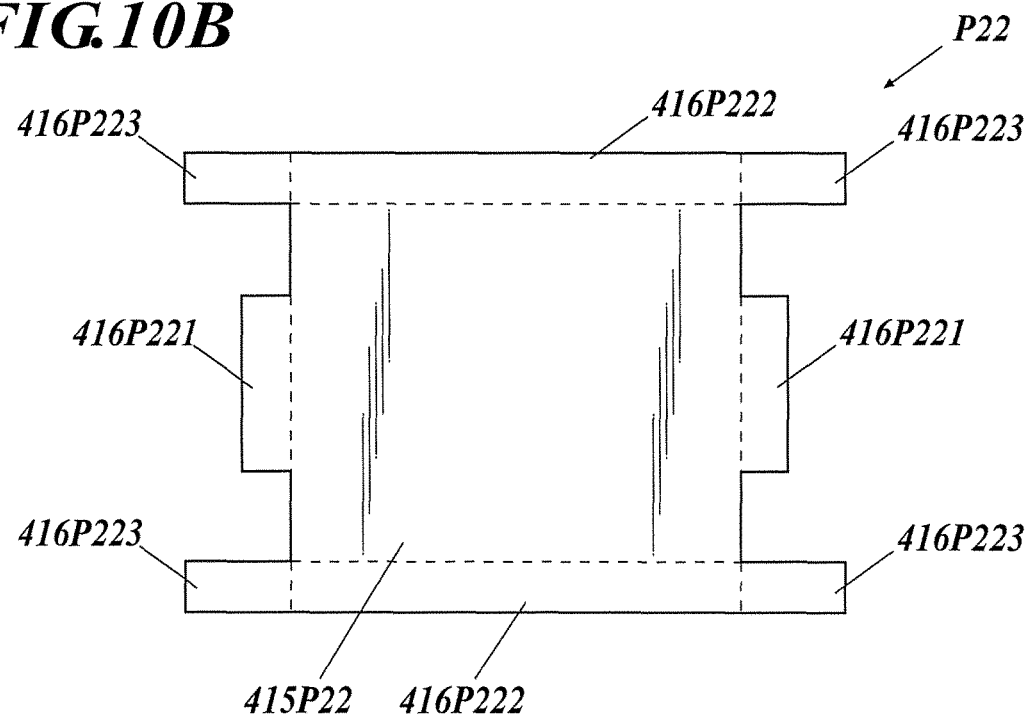
FIG. 10B is a plan view of a second part of yet another combination of CFRP sheet for forming the front plate, in accordance with one or more embodiments.

FIG. 10A and FIG. 10B illustrate the nets of parts P1, P22 of CFRP sheet for forming the front plate 41.

When the parts P1, P22 are used, the front plate 41 also has a three-layer structure with uniform thickness of the incident plate 415 and the side walls 416.

The part P1 is identical to the above-described part P1, and the description thereof is omitted.

The part P22 includes:

a rectangular incident plate forming part 415P22 that forms the incident plate 415 of the front plate 41;

side wall center forming parts 416P221 that are continuously adjacent respectively to mutually opposed two sides of the incident plate forming part 415P22 to form the center parts of the side walls 416;

side wall forming parts 416P222 that are continuously adjacent respectively to the other two sides of the incident plate forming part 415P22 to form the side walls 416; and side wall end forming parts 416P223 that are continuously adjacent respectively to the both ends of the side wall forming parts 416P222 to form the adjacent ends of two side walls 416 adjacent across a corners 417.

Further, the part P22 is formed such that the layered carbon fiber is oriented parallel to the long and short sides of the incident plate forming part 415P22.

To form the front plate 41, one part P22 is laminated under the incident plate forming parts 415P1 of two parts P1.

Since the two side wall center forming parts 416P221 are continuously adjacent to the center parts of the mutually opposed two sides of the incident plate forming part 415P22, they can be vertically erected with respect to the incident plate forming part 415P22 by bending them along the two sides.

Further, since the two side wall forming parts 416P222 are continuously adjacent to the other mutually opposed two sides of the incident plate forming part 415P22, they can be vertically erected with respect to the incident plate forming part 415P22 by bending them along the two sides.

Further, when the two side wall forming parts 416P222 are erected and the side wall end forming parts 416P223 are bent along the creases in the direction perpendicular to the respective longitudinal direction, the side wall end forming parts 416P223, continuously adjacent to both ends of the two side wall forming parts 416P222 are located at both sides of the two side wall center forming parts 416P221 and aligned with the side wall center forming parts 416P221 in the same planes.

By the above-described shaping, the part P22 can be formed into the same three-dimensional shape as the parts P1, and the front plate 41 can be formed by laminating it with the two parts P1 and subjecting them to autoclave molding or heat pressing.

Also in this example, the corners 417 can be formed to have the same cross-sectional structure as illustrated in FIG. 5A, and the incident plate 415 and the side walls 416 can be formed to have a uniform wall thickness.

The above-described examples of parts merely illustrate some of the examples, and the present invention is not limited thereto.

In a corner 417 of the front plate 41, it is possible to use any part that can provide at least one carbon fiber layer that is oriented in the direction from one to the other of side walls 416 adjacent across the corners 417 and that is continuous in the area of the corners 417.

In the case 40 of the radiographic imaging apparatus 1, a breakpoint B where carbon fiber layers are discontinuous over the entire thickness in the wall thickness direction is not formed in the areas of the corners 417 of the front plate 41. Accordingly, the corners 417 have the tensile strength of the carbon fiber layer. This enables an improvement of the strength of the corners 417 of the case 40 that are likely to be subjected to a drop impact and the like.

The corners 417 include a carbon fiber layer that is continuous over the entire areas of the corners 417. This enables a further improvement of the strength over the entire corners 417.

A deformation or damage of the case causes intrusion of light that results in inability to obtain a fine image, a damage of an inner component that makes impossible to take an image, deformation that results in inability to be housed in a photography table or a grid, and loss of the function of the waterproof packing, a shielding gasket, adhesive or the like intervened between the front plate and the back plate. However, by improving the strength of the corners 417, these occurrences are prevented or reduced.

In all four corners 417, a breakpoint B is eliminated, and a carbon fiber layer that is continuous over the entire areas of the corners 417 is provided. This enables an improvement of the strength of all four corners 417 and the protection from an impact.

Elimination of a breakpoint B or provision of a carbon fiber layer continuous over the entire area of a corner 417 may be achieved only in some of the corners 417 in order to protect a particular corner 417.

When a corner of the case 40 composed of the front plate 41 and the back plate 42 is damaged, the entire front plate 41 may have to be replaced. However, by improving the strength of the corners 417, the frequency of replacing the front plate 41 can be reduced.

In the front plate 41, the carbon fiber layers of the incident plate 415 continuously extend to the side walls 416 that are joined to the incident plate 415 as illustrated in FIG. 5B. Accordingly, the tensile strength between the incident plate 415 and the side walls 416 can be retained at a high level, and the chance of collapse of the side walls 416 with respect to the incident plate 415 can be reduced when a corner or an edge is subject to a load. This enables effective protection of the inner components of the case 40.

Since the continuous fiber reinforced resin of the incident plate 415 and the side walls 416 is a carbon fiber reinforced plastic using carbon fiber, the tensile strength is remarkably high. This enables securer protection of the components of the case 40.

Other Arrangements of Parts

The above-described front plate 41 is an example in which the parts P1 constitute two carbon fiber layers that are the second and third layers from the outer side, and the parts P2 and P3 (or the parts P12 and P13 or the part P22) constitute the outermost carbon fiber layer, and this outermost carbon fiber layer is continuous in the corners 417. However, the structure is not limited thereto.

Figure 11A:
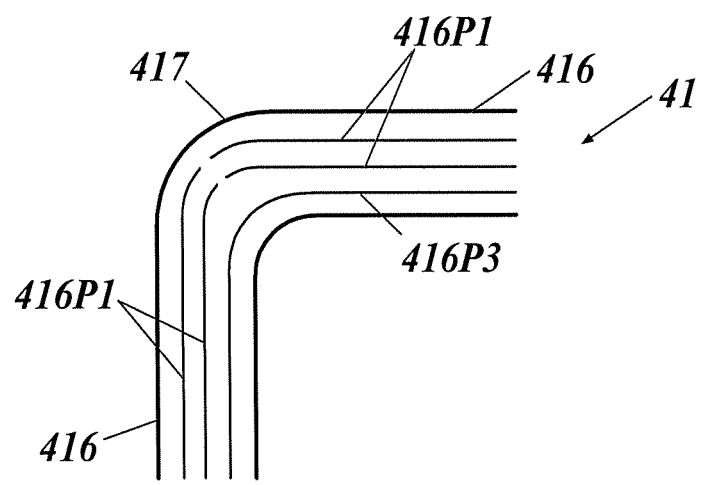
FIG. 11A is a cross-sectional view of a front plate having a layer structure different from that in FIG. 5A and FIG. 5B, taken along the line B-B of FIG. 4B, in accordance with one or more embodiments.
Figure 11B:
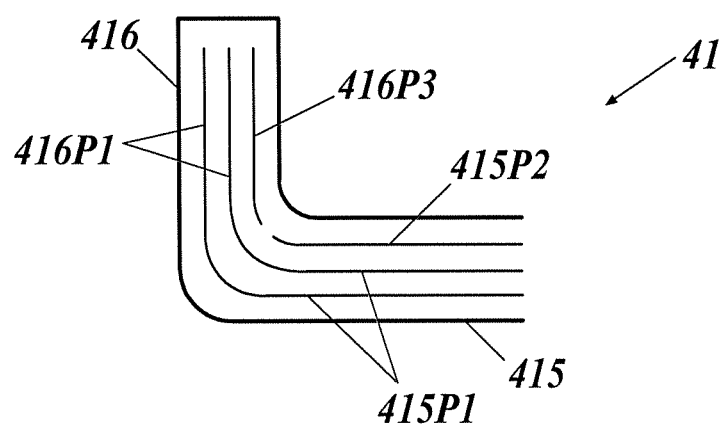
FIG. 11B is a cross-sectional view of the front plate having a layer structure different from that in FIG. 5A and FIG. 5B, taken along the line A-A of FIG. 4A, in accordance with one or more embodiments.

For example, another carbon fiber layer other than the outermost layer may also be continuous in the corners 417 as illustrated in FIG. 11A and FIG. 11B. In the example of FIG. 11A and FIG. 11B, the third (innermost) carbon fiber layer from the outer side is continuous in the corners 417. However, it should be understood well that the second carbon fiber layer from the outer side may be continuous in the corners 417 instead.

In this case, the parts P1 constitute two carbon fiber layers that are the first and second layers from the outer side, and the parts P2 and P3 (or the parts P12 and P13 or the part P22) constitute the third (innermost) carbon fiber layer from the outer side.

Alternatively, the parts P1 may constitute two carbon fiber layers that are the first and third layers from the outer side, and the parts P2 and P3 (or the parts P12 and P13 or the part P22) constitute the second carbon fiber layer from the outer side.

As described above, in order to form a continuous carbon fiber layer in the corners 417, it is necessary to use the side wall forming part 416P3 or the side wall end forming parts 416P13 or 416P223 that are not directly continuously adjacent to the incident plate forming part 415P2, 415P12 or 415P22 of the incident plate 415.

When they are disposed as the first layer from the outer side, a breakpoint where the carbon fiber layer of the incident plate forming part 415P2, 415P12 or 415P22 is discontinuous is likely to be exposed in the surface of the front plate 41. In this case, a smooth shape may not be obtained, a carbon fiber is likely to be exposed in the surface, and a streak may appear in the surface to deteriorate the outer shape.

However, when a carbon fiber layer other than the outermost layer is continuous in the corners 417, these disadvantages can be eliminated.

In the front plate 41, the number of carbon fiber layers is equally three in the incident plate 415 and the side walls 416. However, as long as a carbon fiber layer is continuous in the corners 417, the front plate 41 may be composed of a single layer or multiple layers other than three.

When the front plate 41 is composed of a single layer, it has to be formed only from the parts P2 and P3 or the parts P12 and P13 or the part P22.

When the front plate 41 is composed of multiple layers other than three, the number of layers of the part(s) P1 or of the other parts (the parts P2 and P3 or the parts P12 and P13 or the part P22) can be freely selected from any number of one or more.

According to one or more embodiments, the thickness of the front plate 41 is not uniform between an incident plate 415 and side walls 416, but the side walls 416 are thicker, which will be described referring to the drawings.

Figure 12A:
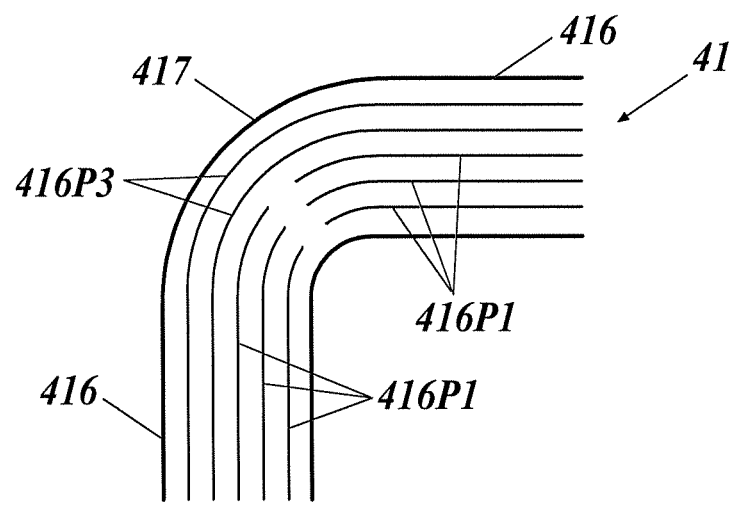
FIG. 12A is a cross-sectional view of a front plate having a layer structure different from that in FIG. 5A and FIG. 5B, taken along the line B-B of FIG. 4B, in accordance with one or more embodiments.
Figure 12B:
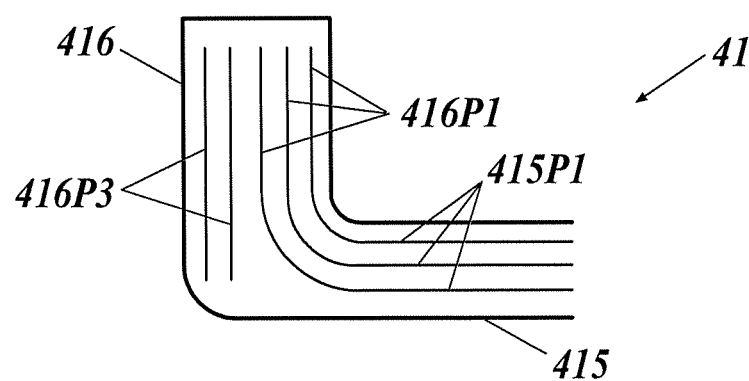
FIG. 12B is a cross-sectional view of the front plate having a layer structure different from that in FIG. 5A and FIG. 5B, taken along the line A-A of FIG. 4A, in accordance with one or more embodiments.

FIG. 12A is a cross-sectional view of the front plate 41 with the side walls 416 thicker than the incident plate 415 taken along the line B-B in FIG. 4B, and FIG. 12B is a cross-sectional view taken along the line A-A in FIG. 4A.

The schematic outer shape of the front plate 41 is identical to that illustrated in FIG. 4A and FIG. 4B.

In the front plate 41 having non-uniform thickness between the incident plate 415 and the side walls 416, the incident plate 415 of the front plate 41 is composed of three carbon fiber layers while the side walls 416 are composed of five carbon fiber layers as illustrated in FIG. 12A and FIG. 12B.

Figure 13A:
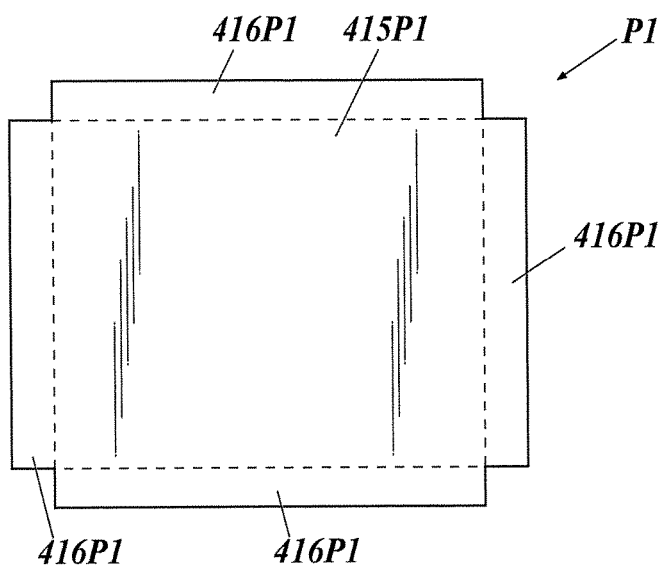
FIG. 13A is a plan view of a first part of yet another combination of CFRP sheet for forming the front plate, in accordance with one or more embodiments.
Figure 13B:
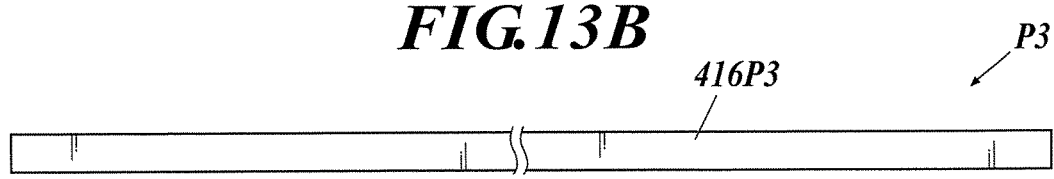
FIG. 13B is a plan view of a second part of yet another combination of CFRP sheet for forming the front plate, in accordance with one or more embodiments.

Further, the front plate 41 is formed from three above-described parts P1 and two above-described parts P3 as illustrated in FIG. 13A and FIG. 13B.

That is, the front plate 41 is formed by laminating the incident plate forming parts 415P1 in the state of the four side wall forming parts 416P1 of three parts P1 being erected, wrapping the two parts P3 around the outer periphery of the erected three side wall forming parts 416P1 and then subjecting them to autoclave molding or heat pressing.

As in the example illustrated in FIG. 5A to FIG. 6C, the parts P3 are wrapped around such that the junctions of one and the other ends of the parts P3 are located outside the areas of the four corners 417.

As illustrated in the cross section in FIG. 12B, three carbon fiber layers oriented in the direction from the incident plate 415 to the side walls 416 are formed in the corners 417 of the front plate 41. Since the three carbon fiber layers are derived from the continuous carbon fiber layers of the incident plate forming parts 415P1 and the side wall forming parts 416P1 of the parts P1, they are all continuous.

Further, as illustrated in FIG. 12A, five carbon fiber layers are laid in the corners 417 in the direction from one to the other of adjacent side walls 416 across a corner 417. Among them, the inner three carbon fiber layers are discontinuous at the corners 417 since all of them are derived from two side wall forming parts 416P1 of the parts P1.

In contrast, the outer two layers are continuous in the entire areas of the corners 417 since all of them are derived from the parts P3.

Also in this front plate 41, a breakpoint B where the carbon fiber layers are discontinuous over the entire thickness in the wall thickness direction is not formed in the areas of the corners 417, and some carbon fiber layers are continuous over the entire areas of the corners 417. This enables an improvement of the strength of the entire corners 417.

In the front plate 41, the side walls 416 are thicker than the incident plate 415 that is joined to the side walls 416. Accordingly, portions including the corners 417 that are likely to be subjected to an external impact can be specifically reinforced. This enables more effective protection of the radiographic imaging apparatus 1 while avoiding a weight increase.

For example, even when the case 40 is subjected to a bending load with two-side support (a load that acts to fold the rectangular incident plate 415 of the case 40 into two), the case 40 sufficiently withstands the load thank to the reinforced side walls 416. This can reduce the occurrence of damage or breakage.

The carbon fiber layers that are continuous over the entire areas of the corners 417, i.e. the carbon fiber layers of the side wall forming parts 416P3 of the parts P3 oriented in the longitudinal direction thereof do not extend to the incident plate 415 but are discontinuous to the incident plate 415. Accordingly, it is possible to readily adjust the number of layers of the carbon fiber layers in the side walls 416 by changing the number of parts P3, which enables adjustment of the strength of the front plate 41.

The number of carbon fiber layers in the incident plater 415 and the side walls 416 can be freely changed as long as the number of carbon fiber layers in the side walls 416 is larger than that in the incident plate 415.

Further, in the corners 417, the carbon fiber layers that are continuous over the entire areas of the corners 417 may be located in any layer, and the number of the layers may also be changed.

In the front plate 41 having the cross-sectional structure as illustrated in FIG. 5A and FIG. 5B or FIG. 12A and FIG.

12B, a carbon fiber layer in the corners 417 is continuous over the entire area of the corners 417. However, it is not always necessary to provide such a carbon fiber layer that is continuous over the entire areas of the corners 417 as long as a breakpoint B where the carbon fiber layers are discontinuous over the entire thickness in the wall thickness direction is not present in the areas of the corners 417.

According to one or more embodiments, a front plate 41 that does not include a carbon fiber layer that is continuous over the entire areas of the corners 417, which will be described below.

The schematic outer shape of the front plate 41 is identical to that illustrated in FIG. 4.

Figure 14A:
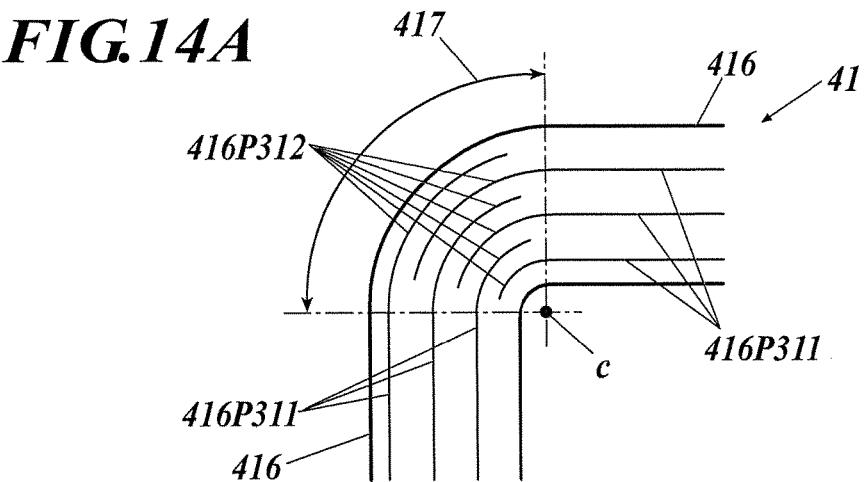
FIG. 14A is a cross-sectional view of a front plate having a layer structure different from that in FIG. 5A and FIG. 5B, taken along the line B-B of FIG. 4B, in accordance with one or more embodiments.
Figure 14B:
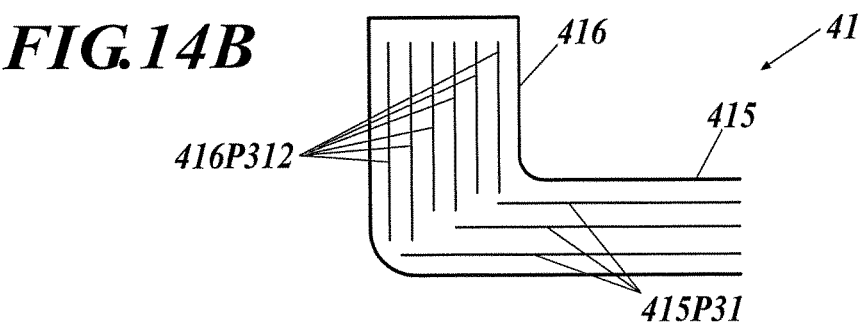
FIG. 14B is a cross-sectional view of the front plate having a layer structure different from that in FIG. 5A and FIG. 5B, taken along the line C-C of FIG. 4A, in accordance with one or more embodiments.

FIG. 14A is a cross-sectional view of the front plate 41 taken along the line B-B in FIG. 4B, and FIG. 14B is a cross-sectional view taken along the line C-C in FIG. 4A.

Figure 15:
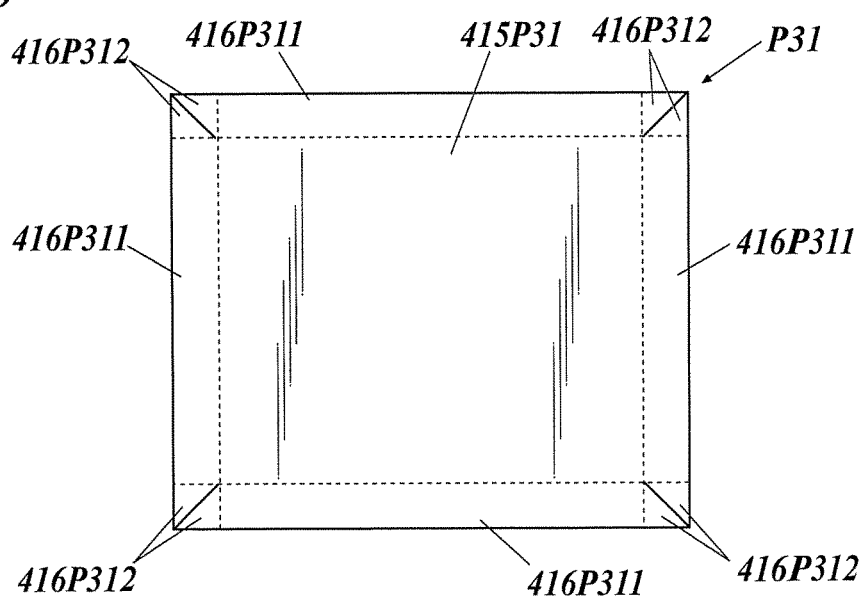
FIG. 15 is a plan view of another part of CFRP sheet for forming the front plate, in accordance with one or more embodiments.

This front plate 41 is formed from two or more (e.g. three) parts P31 of CFRP sheet as illustrated in FIG. 15.

Each of the parts P31 is constituted by a rectangular CFRP sheet that is larger than an incident plate 415 by approximately twice the height of side walls 416, and diagonal slits are formed in the respective corners in an angle of 45°.

The part P31 includes:

a rectangular incident plate forming part 415P31 that forms the incident plate 415 of the front plate 41;

side wall forming parts 416P311 that are continuously adjacent respectively to the tour sides of the incident plate forming part 415P31 and that form side walls 416; and triangular side wall coupling parts 416P312 that are continuously adjacent to both ends of the side wall forming parts 416P311 and that are each laminated with an adjacent end of the side wall forming part 416P311 of another side wall 416 adjacent across a corner 417.

Further, the parts P31 are formed such that the layered carbon fiber is oriented parallel to the long and short sides of the incident plate forming part 415P31.

To form the front plate 41, the parts P31 are bent along the four sides of the incident plate forming parts 415P31 so that the side wall forming parts 416P311 are vertically erected with respect to the incident plate forming parts 415P31.

Then, a side wall coupling part 416P312 continuously adjacent to one of adjacent side wall forming parts 416P311 is bent and laminated on the outer face of the other of the adjacent side wall forming parts 416P311. Further, a side wall coupling part 416P312 continuously adjacent to the other of the adjacent side wall forming parts 416P311 is bent and laminated on the inner face of one of the adjacent side wall forming parts 416P311. A corner is thus formed. The four corners are formed in the same way by bending the corresponding parts so that the front plate 41 is shaped.

The parts P31 are formed into the shape of the front plate 41 one by one sequentially from the innermost part P31, in which a part P31 thus formed into the shape of the front plate 41 is laminated on the outer side of the inner part P31. All three parts P31 are thus formed and laminated in the shape of the front plate 41.

Then, the front plate 41 can be formed by subjecting them to autoclave molding or heat pressing.

When the front plate 41 is formed from the above-described parts P31, the side wall coupling parts 416P312 are overlapped with each other in the corners 417. When the inner side of the corners 417 is formed in an arcuate shape with rather large curvature radius, the overlapped width of the side wall coupling parts 416P312 is narrowed, and they are overlapped only within the areas of the corners 417 which have the shape of an arc (circular sector) in an angle of 90° about the reference points c as illustrated in FIG. 14B.

In this case, the carbon fiber layers in the side wall coupling parts 416P312 oriented in the longitudinal direction of the side walls 416 do not extend over the entire areas of the corners 417, and no carbon fiber layer is continuous over the entire areas of the corners 417 accordingly.

However, a breakpoint B where the carbon fiber layers are discontinuous over the entire thickness in the wall thickness direction is not present in the areas of the corners 417, and no part has strength that is only based on the tensile strength of thermoset resin accordingly. This enables obtaining an effect of improving the strength of the corners 417 based on the tensile strength of the carbon fiber layers and thereby reinforcement of the front plate 41.

The front plate 41 can be formed only from the parts P31 that are constituted by rectangular CFRP sheets with diagonal cuts at the corners. Accordingly, it is possible to reduce the amount of waste sheet. This enables a reduction of the material consumption and the production cost.

In the front plate 41 in which no carbon fiber layer is continuous over the entire areas of the corners 417, the number of carbon fiber layers in the incident plate 415 and the side walls 416 can be selected freely by changing the number of parts P31 used.

Other Examples of Sheet Material of Parts for Forming Front Plate

The above described embodiments illustrate examples in which the sheet material of the parts is fabric of carbon fiber filaments that are woven in a grid pattern in mutually perpendicular two directions and that are impregnated with epoxy resin. Instead of mutually perpendicular two directions, the sheet material may be fabric that is woven in non-perpendicular two directions or three or more intersecting directions.

Alternatively, the front plate 41 may be molded from a sheet material in which carbon fiber filament oriented in a single direction is disposed in a planar shape.

The sheet material with carbon fiber oriented only in a certain direction has high tensile strength in the direction of the carbon fiber but low tensile strength in other directions, such as a perpendicular direction.

Since the sheet material with carbon fiber oriented only in a certain direction includes fiber oriented in a single direction, the tensile strength in the fiber direction is higher than the tensile strength of bidirectional fabric in relation to the thickness, which is approximately twice as high as the tensile strength of a bidirectional fabric when compared in the same thickness.

Further, since a step of forming carbon fiber fabric is not required in the production of the sheet material, it can be produced at low cost.

In view of these properties, it is desirable that the sheet material with carbon fiber oriented only in a certain direction is used in a part that requires high tensile strength only in a single direction.

For example, when the front plate 41 as illustrated in FIG. 4A and FIG. 4B is formed from the above-described combination of the parts P1 and P3, it is desirable that the part P3 for reinforcing the side walls 416 is made of sheet material with carbon fiber oriented only in a certain direction. In this case, the part P3 is formed such that the longitudinal direction of the part P3 corresponds to the orientation direction of the carbon fiber.

Figure 16A:
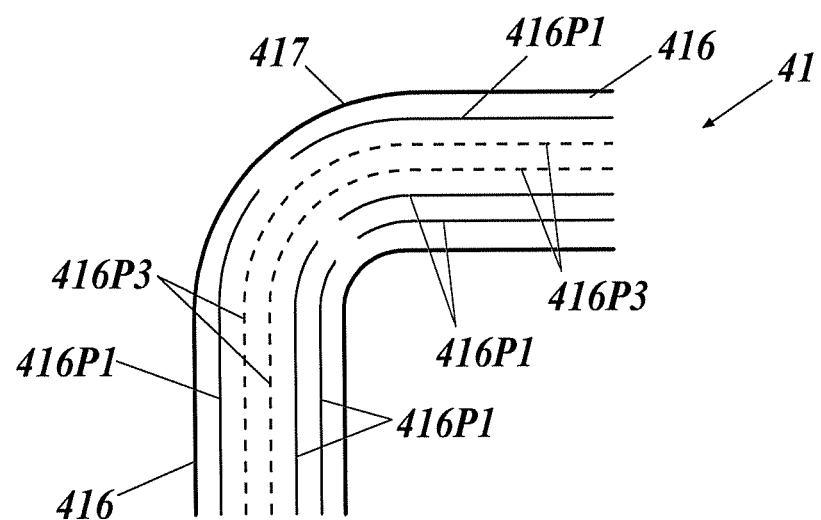
FIG. 16A is a cross-sectional view of a front plate having a layer structure different from that in FIG. 5A and FIG. 5B, taken along the line B-B of FIG. 4B, in accordance with one or more embodiments.
Figure 16B:
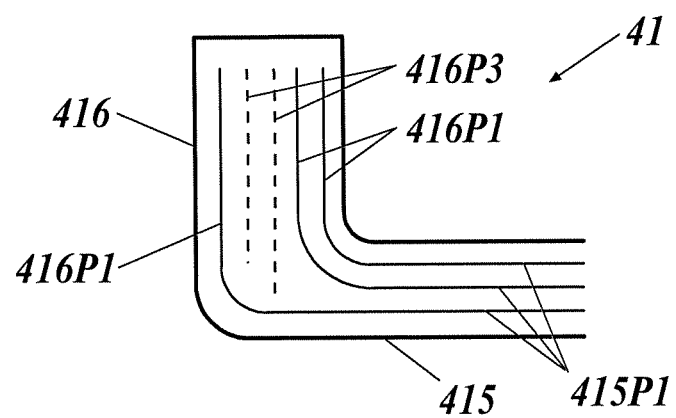
FIG. 16B is a cross-sectional view of the front plate having a layer structure different from that in FIG. 5A and FIG. 5B, taken along the line A-A of FIG. 4A, in accordance with one or more embodiments.

FIG. 16A is a cross-sectional view of the front plate 41 thus formed, taken along the line B-B in FIG. 4B, and FIG. 16B is a cross-sectional view taken along the line A-A in FIG. 4A.

When the front plate 41 is formed only from the above-described part P1, the strength is deteriorated due to breakpoints B formed in the corners 417 (see FIG. 7). In contrast, the side walls 416 of the front plate 41 in FIG. 16 includes the part P3 that is made of sheet material with carbon fiber oriented only in a certain direction, and a carbon fiber layer can be continuous over the entire areas of the corners 417 in the corners 417. This enables a reinforcement of the corners 417.

Further, since the side walls 416 include the part P3 that is made of sheet material with carbon fiber oriented only in a certain direction, the same strength as a bidirectional fabric sheet can be achieved with approximately a half thickness. This enables a reduction of the wall thickness of the side walls 416 and a reduction of the weight and the production cost of the front plate 41.

Blocks Attached to Corners

Blocks 45, which are independent members from the corners 417, may be attached to the outer side of the protrusions of the corners 417 of the front plate 41.

In this example, the blocks 45 are attached to the corners 417 of the front plate 41 of FIG. 12A and FIG. 12B. However, they may be attached to other examples of the front plate 41.

Figure 17A:
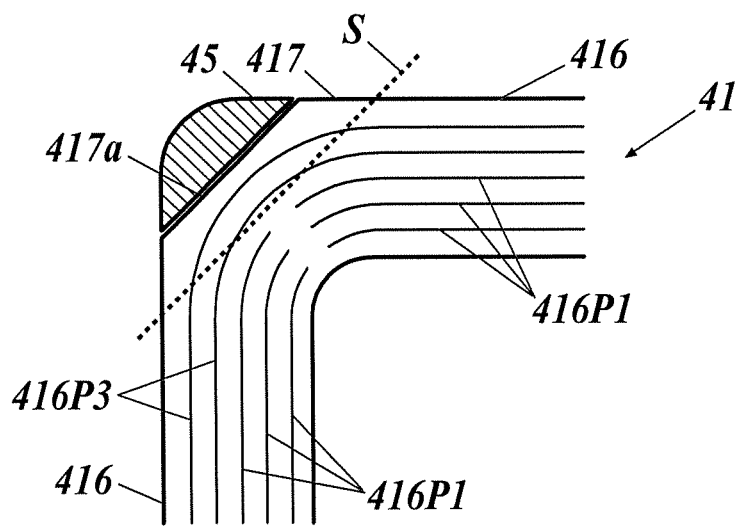
FIG. 17A is a cross-sectional view of a front plate with blocks in the corners, taken along the line B-B in FIG. 4B, in accordance with one or more embodiments.
Figure 17B:
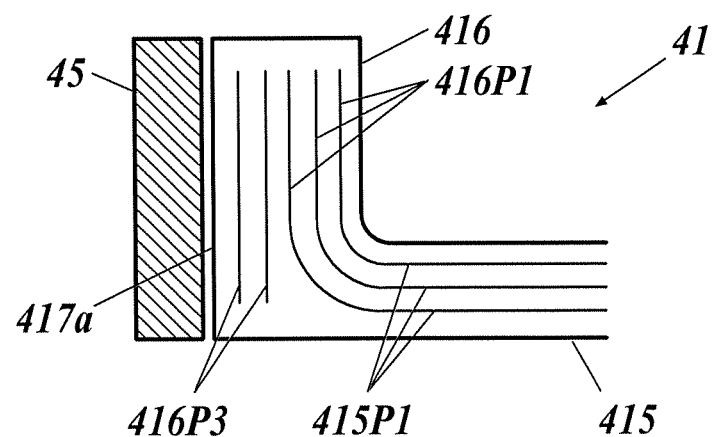
FIG. 17B is a cross-sectional view of the front plate with the blocks in the corners, taken along the line C-C in FIG. 4A, in accordance with one or more embodiments.

FIG. 17A is a cross-sectional view of the front plate 41 with the blocks 45 taken along the line B-B in FIG. 4B, and FIG. 17B is a cross-sectional view taken along the line C-C in FIG. 4A.

The blocks 45, which follow the original shape of the protrusions of the corners 417 of the front plate 41, are attached on the flat faces 417a that are formed by chamfering the protrusions of the corners 417 of the front plate 41. The blocks 45 are fixed to the corners 417 desirably in a detachable and replaceable manner such as screwing. However, they may also be fixed by bonding.

The blocks 45 may be made of the same material as the front plate 41 or a material having different properties from the front plate 41 such as materials with higher strength, higher impact resistance, higher abrasion resistance or higher impact absorption.

When the corners 417 of the front plate 41 are subjected to a drop impact or the like, only the blocks 45 are damaged so that the corners 417 themselves are protected. This facilitates repairing the front plate 41 since it is necessary to replace only the damaged blocks 45.

Further, suitable selection of the material of the blocks 45 can provide advantageous effects according to the properties of the material. For example, the blocks 45 may be formed from a material with higher strength than the front plate 41 to protect the corners 417 more securely. Further, the blocks 45 may be formed from a material other than continuous fiber reinforced resin so that inner resin does not pop out from the surface even when they are damaged.

The flat faces 417a for attaching the blocks 45 are formed in the protrusions of the corners 417 by cutting. For example, when the protrusions are cut to the line S, a carbon fiber layer in the corners 417 is cut, which may cause deterioration of the strength of the corners 417. In particular, when a carbon fiber layer that is continuous over the entire areas of the corners is located at the outer side as in the front plate 41 of the illustrated example, the strength of the corners 417 is decreased to a large degree. Therefore, it is desirable that the flat faces 417a are formed within the range in which a carbon fiber layer is not damaged.

Other Examples of Case

The above-described case 40 is an example in which the front plate 41 is made of continuous fiber reinforced resin. Instead, the entire back plate 42 may be made of continuous fiber reinforced resin, and the back plate 42 may include a bottom plate 425 having the same structure as the incident plate 415 of the front plate 41 and side walls 426 having the same structure as the side walls 416 of the front plate 41.

In this case, the front plate 41 may have the structure as illustrated in FIG. 4A and FIG. 4B. Alternatively, the front plate 41 may be composed only of an incident plate 415 and not include side walls 416.

The above-described case 40 is an example that is composed of the front plate 41 and the back plate 42. However, the structure is not limited thereto.

Figure 18A:
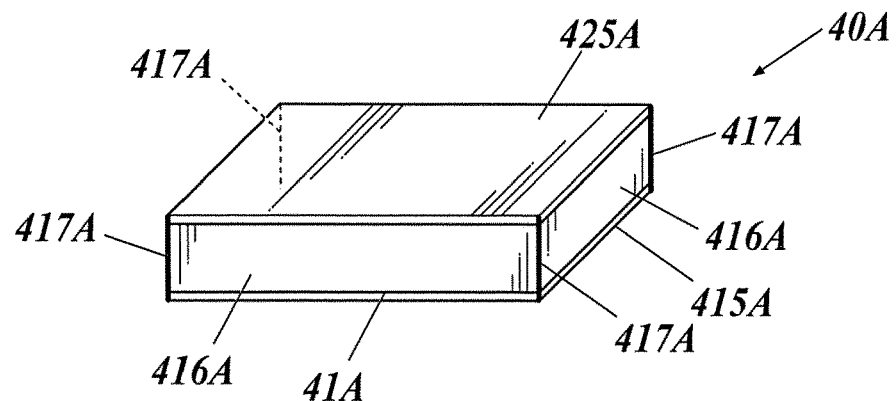
FIG. 18A is a perspective view of another example of the case, in accordance with one or more embodiments.

For example, a case 40A as illustrated in FIG. 18A is composed of three parts of a rectangular cylinder 41A that integrally includes four side walls 416A, an incident plate 415A and a bottom plate 425A.

In this case, it is desirable that a breakpoint B is not present in the four corners 417A of the cylinder 41A as in FIG. 5A, and it is more desirable that one or more of the carbon fiber layers are oriented in the direction from one to the other of side walls 416A adjacent across a corner 417A and are continuous over the entire areas of the corners 417A.

Figure 18B:
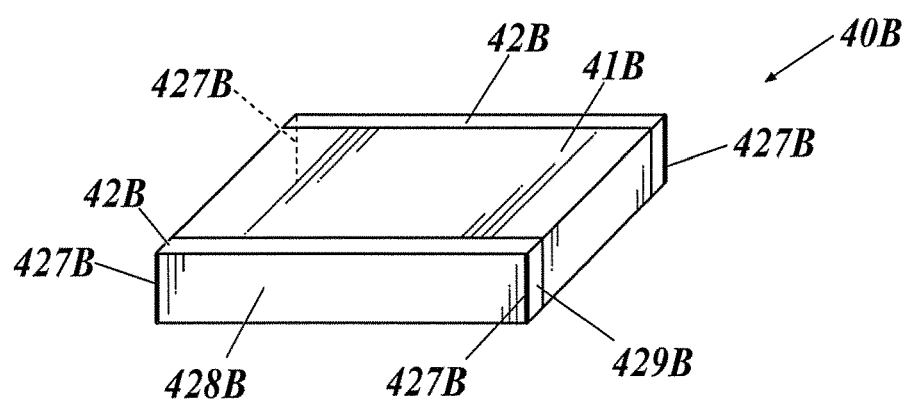
FIG. 18B is a perspective view of another example of the case, in accordance with one or more embodiments.

For another example, a case 40B as illustrated in FIG. 18B is composed of three parts of a flat rectangular cylinder 41B and two lids 42B that respectively close one and the other openings of the cylinder 41B.

In this case, corners 427B are formed at both ends of the lids 42B. It is desirable that a breakpoint B is not present in the areas of all four corners 427B as in FIG. 5A, and it is more desirable that one or more carbon fiber layers are oriented in the direction from a side wall 428B to another side wall 429B adjacent across a corner 427B and are continuous over the entire areas of the corners 427B.

Figure 18C:
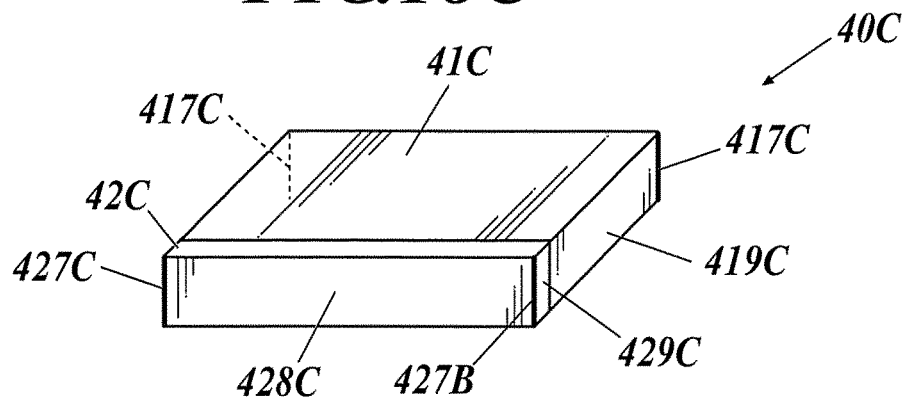
FIG. 18C is a perspective view of another example of the case, in accordance with one or more embodiments.

For yet another example, a case 40C as illustrated in FIG. 18C is composed of two parts of a flat rectangular cylinder 41C and a lids 42C that closes one opening of the cylinder 41C.

The cylinder 41C is open at one end and closed at the other end.

In this case, corners 427C are formed at both ends of the lid 42C. It is desirable that a breakpoint B is not present in the areas of all corners 427C as in FIG. 5A, and it is more desirable that one or more carbon fiber layers are oriented in the direction from a side wall 428C to another side wall 429C adjacent across a corner 427C and are continuous over the entire areas of the corners 427C.

Similarly, corners 417C are formed at both ends of the closed end of the cylinder 41C. It is desirable that a breakpoint B is not present in the areas of all corners 417C as in FIG. 5A, and it is more desirable that one or more carbon fiber layers are oriented in the direction from a side walls 419C to another side wall (not shown) adjacent across a corner 417C and are continuous over the entire areas of the corners 417C.

Others

The fiber of the above-described continuous fiber reinforced resin is not limited to carbon fiber and may be other fibers (e.g. glass fiber) that improve the strength of the resin. Further, the resin added to the fiber is not limited to epoxy resin, and may be other thermoset resins or plastic resins.

The present invention is not limited to the above-described embodiments, and suitable changes can be made without departing from the features of the present invention.

Although the disclosure has been described with respect to only a limited number of embodiments, those skilled in the art, having benefit of this disclosure, will appreciate that various other embodiments may be devised without departing from the scope of the invention. Accordingly, the scope of the invention should be limited only by the attached claims.

What is claimed is:

1. A portable radiographic imaging apparatus; comprising:
   a sensor panel comprising two-dimensionally arrayed radiation detector elements; and
   a case that houses the sensor panel, wherein:
   the case comprises a front member or a back member that is composed of resin sheet material and that comprises a first part and a second part,
   the first part comprises:
      a rectangular incident plate forming part that forms an incident plate where radiation is incident; and
      four side wall forming parts that continue from four sides of the incident plate forming part, respectively, and are bent to form four side walls,
   the second part has a strip shape and covers at least one of a plurality of corners where two of the side walls are adjacent,
   the side walls are made of a continuous fiber reinforced resin that comprises fiber layers oriented in a predetermined direction,
   the fiber layers are oriented in a direction from one to the other of the adjacent side walls in the at least one of the corners, and
   no breakpoint exists in an area of the at least one of the corners, wherein the breakpoint is where the fiber layers are discontinuous over an entire thickness in a wall thickness direction.

2. The portable radiographic imaging apparatus according to claim 1, wherein no breakpoint exists in any of the corners.

3. The portable radiographic imaging apparatus according to claim 1, wherein at least one of the fiber layers is continuous over an entire area of the at least one of the corners.

4. The portable radiographic imaging apparatus according to claim 3, wherein at least one of the fiber layers is continuous over an entire area of all the corners.

5. The portable radiographic imaging apparatus according to claim 3, wherein:
   at least two of the fiber layers are laminated in the wall thickness direction in the at least one of the corners, and
   the fiber layer that is continuous over the entire area of the at least one of the corners is not an outermost layer of the laminated fiber layers.

6. The portable radiographic imaging apparatus according to claim 3, wherein the fiber layer that is continuous over the entire area of the at least one of the corners is oriented only in the predetermined direction.

7. The portable radiographic imaging apparatus according to claim 1, wherein:
   the case further comprises:
      the front member; and
      the back member comprising a bottom plate opposed to the incident plate.

8. The portable radiographic imaging apparatus according to claim 7, wherein the side walls are thicker than the incident plate or the bottom plate that is joined to the side walls.

9. The portable radiographic imaging apparatus according to claim 7, wherein at least one of the fiber layers is continuous over an entire area of the at least one of the corners and extends to neither the incident plate of the front member nor the bottom plate of the back member.

10. The portable radiographic imaging apparatus according to claim 7, wherein at least one of the fiber layers of continuous fiber reinforced resin of the incident plate or the bottom plate extends to the side walls that are joined to the incident plate or the bottom plate.

11. The portable radiographic imaging apparatus according to claim 1, wherein the continuous fiber reinforced resin is carbon fiber reinforced plastic resin.

12. The portable radiographic imaging apparatus according to claim 1, wherein an independent block is attached to outer sides of protrusions of the at least one of the corners.

13. The portable radiographic imaging apparatus according to claim 12, wherein the block is made of a different material from the at least one of the corners.

14. The portable radiographic imaging apparatus according to claim 1, wherein
   the second part has:
      a length equal to a total length of the side walls in a longitudinal direction; and
      a width equal to a height of the front member.

15. The portable radiographic imaging apparatus according to claim 1, wherein
   the front member further comprises:
      a third part that comprises a rectangular incident plate forming part that forms the incident plate and is laminated on the incident plate forming part of the first part.

* * * * *